(12) United States Patent
Miao et al.

(10) Patent No.: US 11,766,696 B2
(45) Date of Patent: Sep. 26, 2023

(54) BI-LAYER METAL ELECTRODE FOR MICROMACHINED ULTRASONIC TRANSDUCER DEVICES

(71) Applicant: BFLY Operations, Inc., Guilford, CT (US)

(72) Inventors: Lingyun Miao, Fremont, CA (US);
Jianwei Liu, Fremont, CA (US);
Jonathan M. Rothberg, Miami Beach, FL (US)

(73) Assignee: BFLY OPERATIONS, INC., Burlington, MA (US)

( * ) Notice: Subject to any disclaimer, the term of this patent is extended or adjusted under 35 U.S.C. 154(b) by 767 days.

(21) Appl. No.: 16/784,186

(22) Filed: Feb. 6, 2020

(65) Prior Publication Data
US 2020/0254487 A1   Aug. 13, 2020

Related U.S. Application Data

(60) Provisional application No. 62/802,583, filed on Feb. 7, 2019.

(51) Int. Cl.
*B06B 1/00* (2006.01)
*B06B 1/02* (2006.01)
*H10N 30/06* (2023.01)

(52) U.S. Cl.
CPC .......... *B06B 1/0292* (2013.01); *H10N 30/06* (2023.02); *B81B 2201/0271* (2013.01);
(Continued)

(58) Field of Classification Search
CPC ......... B06B 1/0292; H01L 41/29; A61B 8/12; A61B 8/4483; B81C 2201/0101;
(Continued)

(56) References Cited

U.S. PATENT DOCUMENTS

| 9,067,779 B1 | 6/2015 | Rothberg et al. |
| 9,499,392 B2 | 11/2016 | Rothberg et al. |

(Continued)

FOREIGN PATENT DOCUMENTS

WO   WO 2017/222964 A1   12/2017

OTHER PUBLICATIONS

International Search Report and Written Opinion dated Apr. 30, 2020 in connection with International Application No. PCT/US2020/017013.
(Continued)

*Primary Examiner* — Paul D Kim
(74) *Attorney, Agent, or Firm* — Osha Bergman Watanabe & Burton LLP (57) ABSTRACT

A method of forming an ultrasonic transducer device includes forming a patterned metal electrode layer over a substrate, the patterned metal electrode layer comprising a lower layer and an upper layer formed on the lower layer; forming an insulation layer over the patterned metal electrode layer; and planarizing the insulation layer to the upper layer of the patterned metal electrode layer, wherein the upper layer comprises a electrically conductive material that serves as a chemical mechanical polishing (CMP) stop layer that has CMP selectivity with respect to the insulation layer and the lower layer, and wherein the upper layer has a CMP removal rate slower than that of the insulation layer.

26 Claims, 6 Drawing Sheets

(52) U.S. Cl.
CPC ... *B81B 2203/0315* (2013.01); *B81B 2203/04* (2013.01); *B81C 2201/0101* (2013.01); *B81C 2201/013* (2013.01); *B81C 2201/0147* (2013.01); *B81C 2201/0174* (2013.01); *B81C 2203/0714* (2013.01)

(58) Field of Classification Search
CPC ...... B81C 2201/013; B81C 2201/0147; B81C 2203/0315; B81C 2203/0714; B81B 2203/0315; B81B 2203/04; B81B 2201/0271
See application file for complete search history.

(56) References Cited

U.S. PATENT DOCUMENTS

| | | | |
|---|---|---|---|
| 9,521,991 | B2 | 12/2016 | Rothberg et al. |
| 9,533,873 | B2 | 1/2017 | Rothberg et al. |
| 9,592,030 | B2 | 3/2017 | Rothberg et al. |
| 10,272,471 | B2 | 4/2019 | Alie et al. |
| 10,497,856 | B2 | 12/2019 | Rothberg et al. |
| 2003/0011283 | A1 | 1/2003 | Takeuchi et al. |
| 2008/0042225 | A1 | 2/2008 | Machida et al. |
| 2011/0055447 | A1 | 3/2011 | Costa |
| 2014/0217478 | A1 | 8/2014 | Rothberg et al. |
| 2014/0264660 | A1 | 9/2014 | Rothberg et al. |
| 2014/0332911 | A1 | 11/2014 | Dirksen et al. |
| 2019/0231312 | A1 | 8/2019 | Fife et al. |
| 2019/0275561 | A1 | 9/2019 | Fife et al. |
| 2019/0336099 | A1 | 11/2019 | Fife et al. |
| 2019/0336103 | A1 | 11/2019 | Fife et al. |
| 2019/0336104 | A1 | 11/2019 | Fife et al. |
| 2020/0013691 | A1 | 1/2020 | Liu et al. |
| 2020/0102214 | A1 | 4/2020 | Liu et al. |
| 2020/0147641 | A1 | 5/2020 | Fife et al. |
| 2020/0156110 | A1* | 5/2020 | Miao ................... B06B 1/0292 |

OTHER PUBLICATIONS

Daft et al., Microfabricated ultrasonic transducers monolithically integrated with high voltage electronics. Proc Ultrason Symp. 2004;493-6.

Gurun et al., Front-end CMOS electronics for monolithic integration with CMUT arrays: circuit design and initial experimental results. Proc Ultrason Symp. 2008;390-3.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

International Preliminary Report on Patentability dated Aug. 19, 2021 in connection with International Application No. PCT/US2020/017013.

* cited by examiner

BI-LAYER METAL ELECTRODE FOR MICROMACHINED ULTRASONIC TRANSDUCER DEVICES

CROSS-REFERENCE TO RELATED APPLICATIONS

This application claims the benefit under 35 U.S.C. § 119(e) of U.S. Provisional Patent Application Ser. No. 62/802,583, filed Feb. 7, 2019, entitled "BI-LAYER METAL ELECTRODE FOR MICROMACHINED ULTRASONIC TRANSDUCER DEVICES," which is hereby incorporated herein by reference in its entirety.

BACKGROUND

The present disclosure relates generally to micromachined ultrasonic transducers and, more specifically, to bi-layer metal electrodes for micromachined ultrasonic transducer cavities and transducer manufacturing techniques.

Ultrasound devices may be used to perform diagnostic imaging and/or treatment, using sound waves with frequencies that are higher than those audible to humans. When pulses of ultrasound are transmitted into tissue, sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasonic transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, generates an output electrical signal.

SUMMARY

In one aspect, a method of forming an ultrasonic transducer device includes forming a patterned metal electrode layer over a substrate, the patterned metal electrode layer comprising a lower layer and an upper layer formed on the lower layer; forming an insulation layer over the patterned metal electrode layer; and planarizing the insulation layer to the upper layer of the patterned metal electrode layer, wherein the upper layer comprises a electrically conductive material that serves as a chemical mechanical polishing (CMP) stop layer that has CMP selectivity with respect to the insulation layer and the lower layer, and wherein the upper layer has a CMP removal rate slower than that of the insulation layer.

In another aspect, an ultrasonic transducer device includes a patterned metal electrode layer disposed on first regions of a substrate, the patterned metal electrode layer comprising a lower layer and an upper layer formed on the lower layer; a planarized insulation layer disposed on second regions of the substrate layer, wherein the upper layer comprises an electrically conductive material that has CMP selectivity with respect to the insulation layer and the lower layer; a cavity defined in a membrane support layer, the membrane support layer formed over the patterned metal electrode layer and the planarized insulation layer; and a membrane bonded to the membrane support layer, and wherein the upper layer has a CMP removal rate slower than that of the insulation layer.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 3-1 through 3-8 are a series of cross-sectional views illustrating the exemplary process flow of FIG. 2.

DETAILED DESCRIPTION

The techniques described herein relate to a bi-layer metal electrode for micromachined ultrasonic transducer cavities.

One type of transducer suitable for use in ultrasound imaging devices is a micromachined ultrasonic transducer (MUT), which can be fabricated from, for example, silicon and configured to transmit and receive ultrasound energy. MUTs may include capacitive micromachined ultrasonic transducers (CMUTs) and piezoelectric micromachined ultrasonic transducers (PMUTs), both of which can offer several advantages over more conventional transducer designs such as, for example, lower manufacturing costs and fabrication times and/or increased frequency bandwidth. With respect to the CMUT device, the basic structure is a parallel plate capacitor with a rigid bottom electrode and a top electrode residing on or within a flexible membrane. Thus, a cavity is defined between the bottom and top electrodes. In some designs (such as those produced by the assignee of the present application for example), a CMUT may be directly integrated on an integrated circuit that controls the operation of the transducer. One way of manufacturing a CMUT is to bond a membrane substrate to an integrated circuit substrate, such as a complementary metal oxide semiconductor (CMOS) substrate. This may be performed at temperatures sufficiently low to prevent damage to the devices of the integrated circuit.

Figure 1:
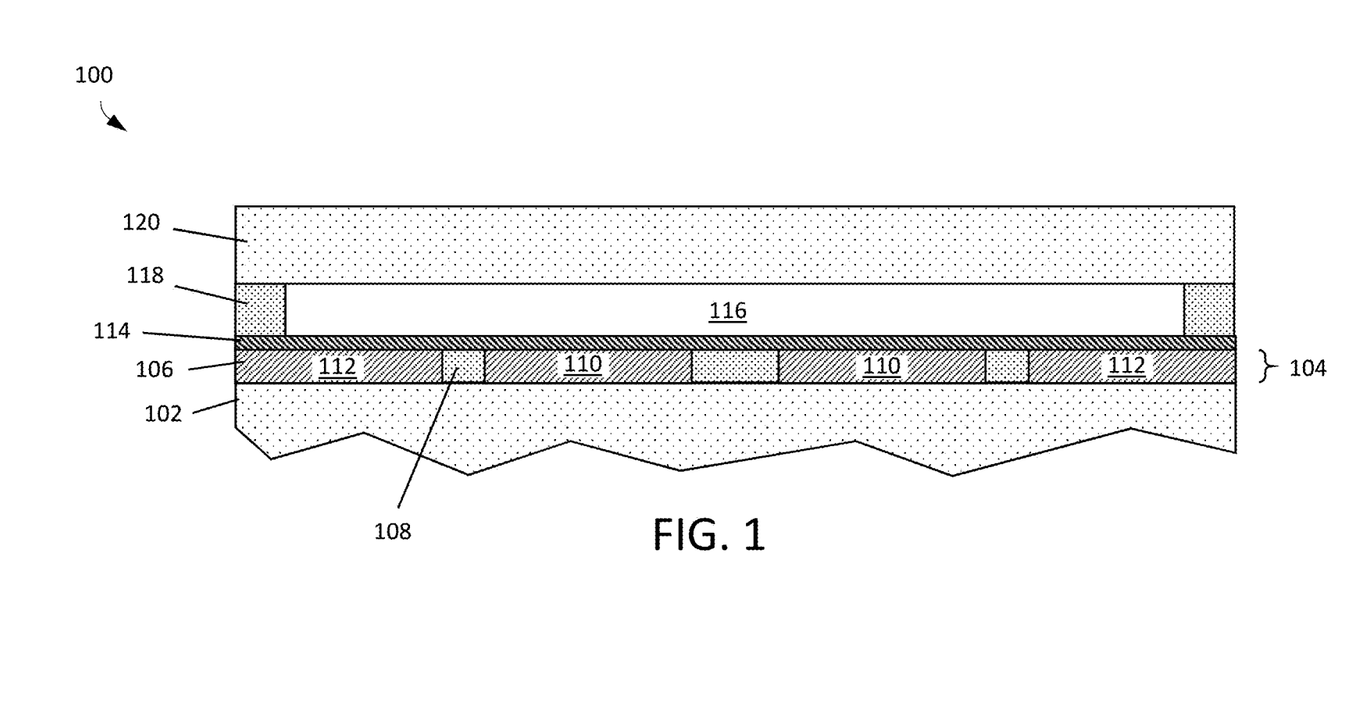
FIG. 1 is a cross-sectional view of an exemplary micromachined ultrasonic transducer device.

Referring initially now to FIG. 1, there is shown a cross-sectional view of an exemplary micromachined ultrasonic transducer device 100, such as a CMUT. The transducer device 100 includes a substrate, generally designated by 102, (e.g., a complementary metal oxide semiconductor (CMOS) substrate, such as silicon) having one or more layers such as for example: CMOS circuits, wiring layers, redistribution layers, and one more insulation/passivation layers. A transducer bottom electrode layer, designated generally at 104, is disposed over the substrate 102 and includes for example patterned metal regions 106 (e.g., titanium (Ti)) and insulation regions 108 (e.g., $SiO_2$). In the illustrated example, portions 110 of the metal regions 106 may serve as a transducer bottom electrode (e.g., in a "donut" or ring configuration), while portions 112 of the metal regions 106 may serve another function (e.g., a bypass metal). As specific substrate and transducer bottom electrode patterns are not the focus of the present disclosure, only a single example is presented in the figures. It will be appreciated, however, that the present embodiments may also be implemented in conjunction with several other transducer electrode structures including (but not limited to), for example: the aforementioned donut shaped electrode pattern (e.g., interior metal removed), multiple segment or ring electrodes, and additional metal patterns used for other purposes besides bottom electrodes (e.g., cavity getter during bonding).

Still referring to FIG. 1, a bottom cavity layer 114 is disposed over the transducer bottom electrode layer 104. The bottom cavity layer 114 may include, for example, a thin film layer stack including an $SiO_2$ layer deposited by chemical vapor deposition (CVD) and an aluminum oxide ($Al_2O_3$) layer deposited by atomic layer deposition (ALD). A transducer cavity 116 is defined by lithographic patterning and etching of a membrane support layer 118 that is formed on the bottom cavity layer 114. The membrane support layer 118 may be an insulating layer, such as $SiO_2$ for example, the remaining portions of which provide a support surface to which a flexible transducer membrane 120 (e.g., highly doped silicon at a concentration of about $1\times10^{18}$ atoms/cm$^3$ to about $1\times10^{19}$ atoms/cm$^3$) is bonded.

In order to preserve the integrity and functionality of the various CMOS devices residing within the substrate 102, a relatively low temperature bonding process (e.g., less than about 450° C.) is employed for bonding the transducer membrane 120 to the membrane support layer 118. Accordingly, it is desirable to have a smooth bonding interface between the bonded surfaces. In one example, a surface roughness less than about 1 nanometers (nm) over a range of 100 microns (μm) may be desirable for this purpose. Thus, chemical mechanical polishing (CMP) may be used during the manufacturing process to planarize the metal regions 106 and insulation regions 108 of the transducer bottom electrode layer 104 to provide a smooth bonding interface for downstream steps.

When a metal electrode layer is formed over a CMOS substrate, such as substrate 102 of FIG. 1, it may be lithographically patterned and etched to form, for example, the pattern illustrated in FIG. 1 (e.g., patterned portions 110 and 112). The insulation regions 108 may then be formed by blanket deposition and overfill of insulation material (e.g., $SiO_2$) followed by CMP removal to expose and planarize the metal patterned portions 110/112. One way to facilitate this part of the manufacturing process may be to form a CMP stop layer (not shown) atop the metal of the bottom electrode metal layer 104 prior to electrode patterning. Following the insulation layer 108 overfill, the CMP stop layer may assist as an endpoint structure as excess oxide material is polished away.

An exemplary material that could be used to cap a Ti bottom metal electrode layer is silicon nitride ($Si_3N_4$). Generally speaking, $Si_3N_4$ has a rate of removal (RR) selectivity on the order of about 10-20× that of $SiO_2$, meaning that as an $SiO_2$ layer is removed from a substrate by a process such as CMP, the same process will begin to remove $Si_3N_4$ only about 10-20 times slower than $SiO_2$. The use of $Si_3N_4$ may therefore require it to be deposited at a greater thickness than desired and may also be somewhat disadvantageous in terms of remaining film thickness uniformity control and therefore the cavity gap control. Moreover, since $Si_3N_4$ is an insulating material instead of a conductive material, and since it can also act as a charge trapping material that may be detrimental to the operation of a CMUT device, it is a sacrificial dielectric CMP stop layer in that it needs to be removed after polishing. This in turn results in a longer process cycle time and possibly even poorer surface roughness due to this extra removal process. On the other hand, without the use of a sacrificial CMP stop layer such as $Si_3N_4$ (e.g., forming the Ti electrode metal alone but at a greater initial thickness and using the Ti material itself as a CMP stop layer for removing $SiO_2$), removal selectivity and surface roughness would be even worse. Moreover, the process would be uncontrollable.

Accordingly, the inventors herein have recognized that it is desirable to incorporate a CMP stop material having a high CMP removal rate (RR) selectivity with respect to oxide and titanium, that results in film thickness uniformity and good surface roughness after polishing, and that has sufficient conductivity so as to allow the material to remain in the structure (i.e., not a sacrificial material). Furthermore, the inventors have recognized that one particularly suitable material for this application is a thin ruthenium (Ru) capping layer formed on top of the Ti electrode metal layer. Such a bi-metal electrode may enable a low cost and high-throughput CMP process to be achieved and further results in good film thickness uniformity and a smooth polishing surface, which is in turn highly advantageous for volume of integrated, on-chip ultrasound transducer devices such as discussed above.

Figures 31, 32:
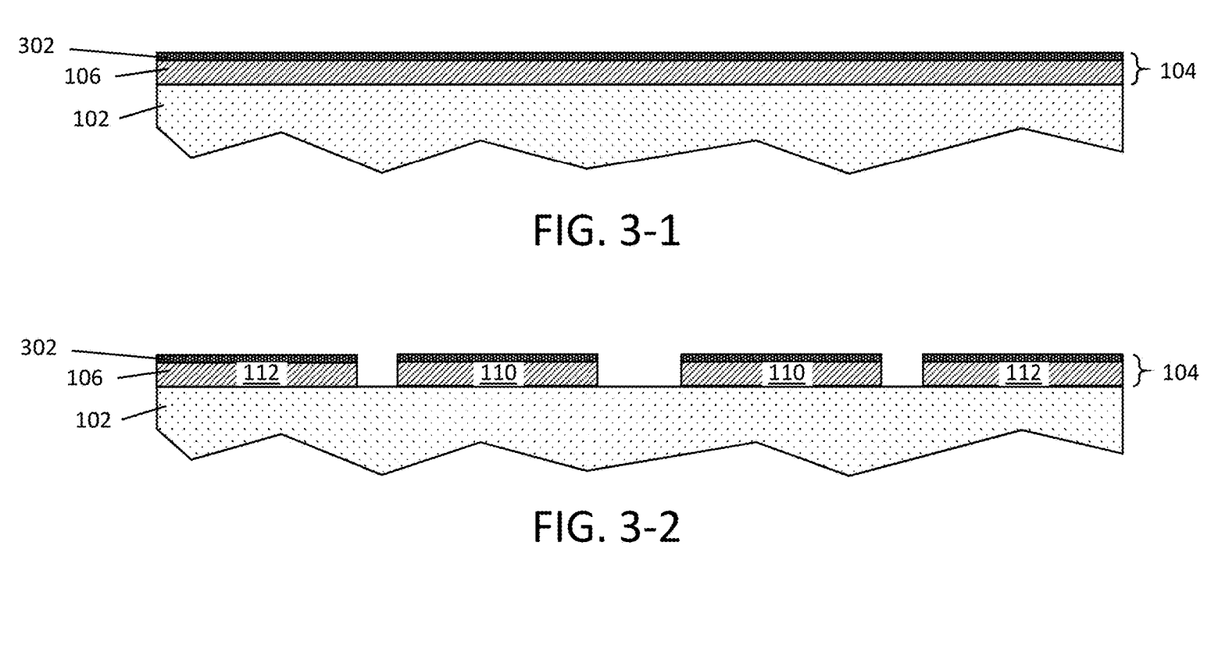

Referring generally now to FIG. 2 and FIGS. 3-1 through 3-8 there is shown, respectively, a flow diagram and a series of cross-sectional views illustrating an exemplary process 200 for forming a micromachined ultrasonic transducer device having a bi-metal electrode layer according to an embodiment. For ease of illustration, like elements in the various figures are designated with like reference numerals where applicable. As indicated in block 202 of FIG. 2 and shown in FIG. 3-1, a bi-metal transducer lower electrode layer (stack) 104 is deposited on a CMOS substrate 102. In an exemplary embodiment, the metal stack 104 may include a Ti layer 106 having a thickness of about 100 nm to about 300 nm formed on the CMOS substrate 102, and a thin Ru CMP stop layer 302 having a thickness of about 10 nm to about 30 nm formed on the Ti layer. Although Ru is a particularly advantageous material for a CMP stop layer due to its high CMP selectivity with respect to oxide and titanium and its electrical conductivity, it is contemplated that other materials could also be used for a CMP stop layer including, but not necessarily limited to, tantalum (Ta). More broadly stated, other materials could also be used for a CMP stop layer provided such materials have a desired CMP RR (e.g., about 100×-200×) that of $SiO_2$, and are not susceptible to charge trapping during CMUT operations.

Figure 2:
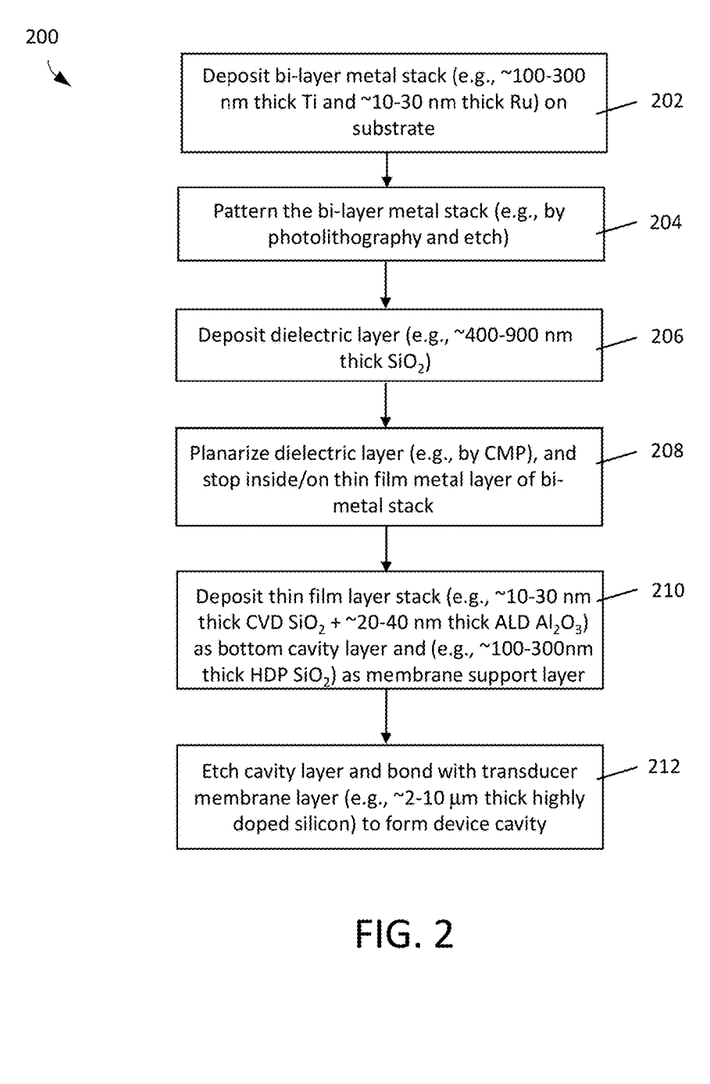
FIG. 2 is a flow diagram describing an exemplary process flow for forming a micromachined ultrasonic transducer device having a bi-layer metal sensing electrode layer according to an embodiment.

Then, as indicated in block 204 of FIG. 2, the bi-metal stack 104 is patterned, e.g., by photolithography and etching, to form the pattern shown in FIG. 3-2. Again, because specific transducer bottom electrode patterns are not the focus of the present disclosure, it will be appreciated that other patterns could be used in accordance with embodiments. As indicated previously, portions 110 of the patterned bi-metal stack 104 may serve as a transducer bottom electrode (e.g., in a "donut" or ring configuration), while portions 112 of the patterned bi-metal stack 104 may serve another function (e.g., a bypass metal).

Figure 33:
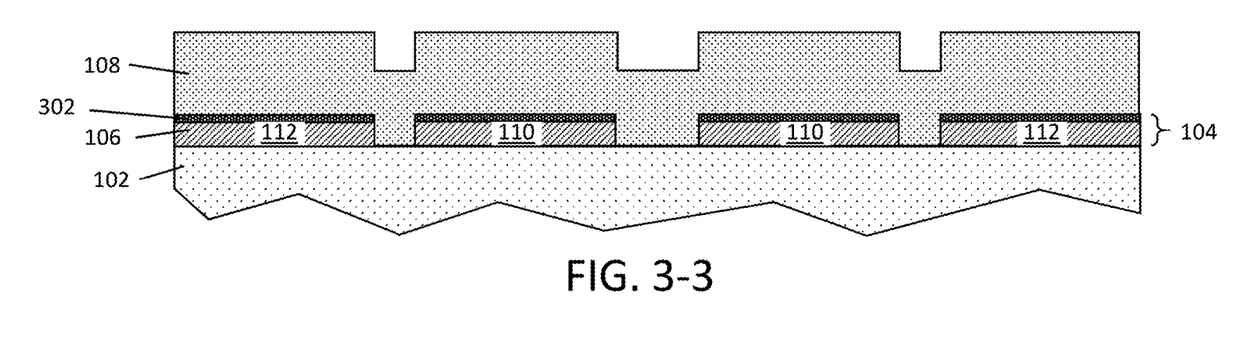
Figure 34:
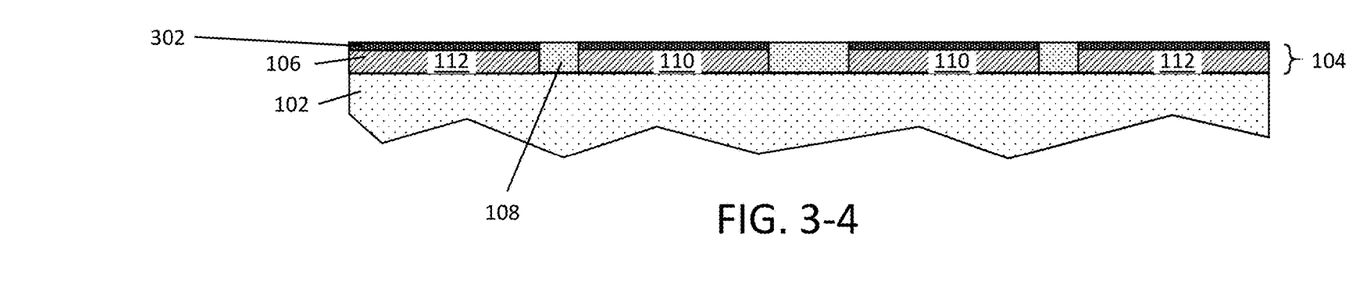

From this point, the process 200 proceeds to block 206 of FIG. 2 where a dielectric material (e.g., $SiO_2$ layer) is formed over the structure so as to fill the regions corresponding to removed bi-metal stack 104 material. In an embodiment, the $SiO_2$ layer 108 may be initially formed at thickness of about 400 nm to about 900 nm, as illustrated in FIG. 3-3. Then, as indicated in block 208 of FIG. 2 and illustrated in FIG. 3-4, the SiO₂ layer 108 is planarized by CMP, stopping on or within the thin film Ru layer 302. Advantageously, the CMP removal selectivity of Ru, which may be on the order of about 200:1 with respect to SiO₂ and about 10×-15× better than that of SiN, allows the layer 302 to be formed at a smaller thickness that SiN. That is, the CMP RR of Ru is about 10-15 times slower with respect to silicon nitride. This in turn may provide improved overall layer thickness uniformity, a tighter transducer cavity gap control, and a smoother interface for better bonding with a transducer membrane. In addition, the exemplary fabrication embodiments may also result in advantages in terms of lower production cost and shorter process cycle time, when compared to alternative approaches, and thus it is particularly suitable for volume manufacturing.

Figure 35:
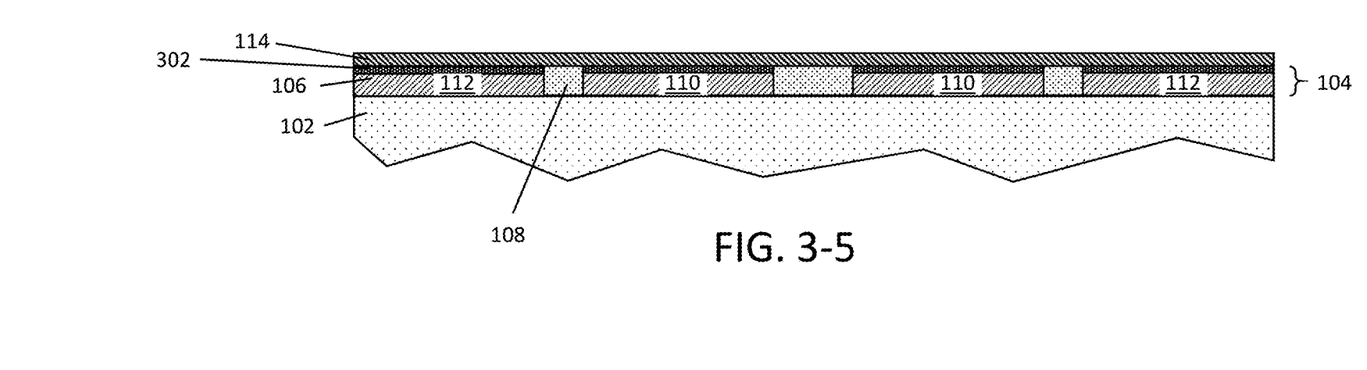
Figure 36:
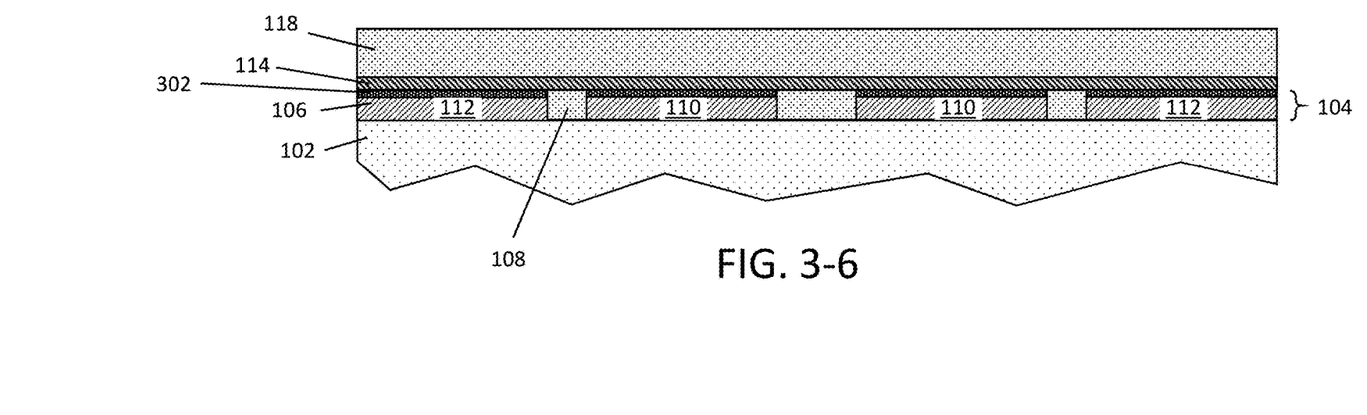

Following device planarization, the process 200 may proceed to block 210 of FIG. 2 for deposition of a thin film layer stack that, as described above, may serve as a bottom cavity layer 114. The bottom cavity layer 114, illustrated in FIG. 3-5, may include for example, a CVD SiO₂ layer formed at a thickness of about 10 nm to about 30 nm and an ALD Al₂O₃ layer formed at a thickness of about 20 nm to about 40 nm. As also indicated in block 210 of FIG. 2 and illustrated in FIG. 3-6, a membrane support layer 118 such as an HDP SiO₂ material is formed at a thickness of about 100 nm to about 300 nm on the bottom cavity layer 114.

Figure 37:
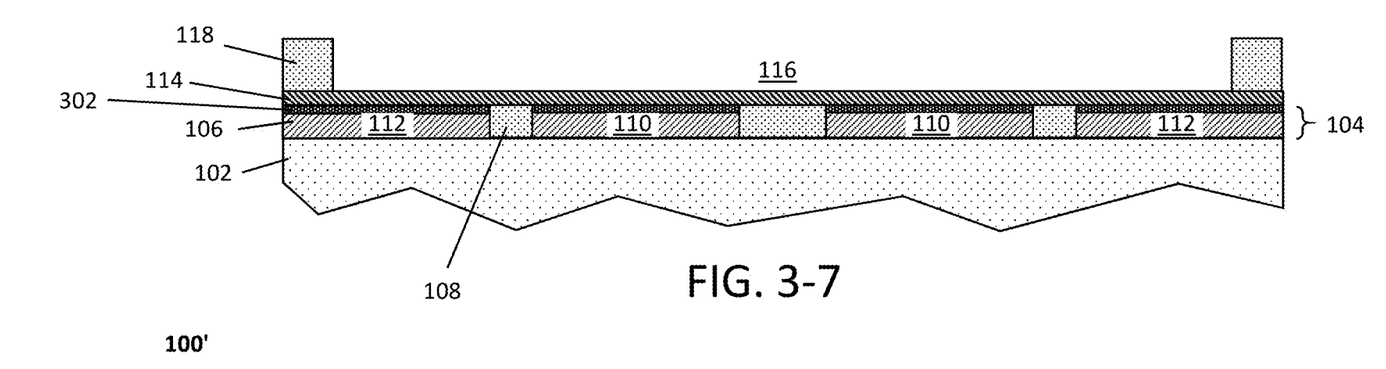
Figure 38:
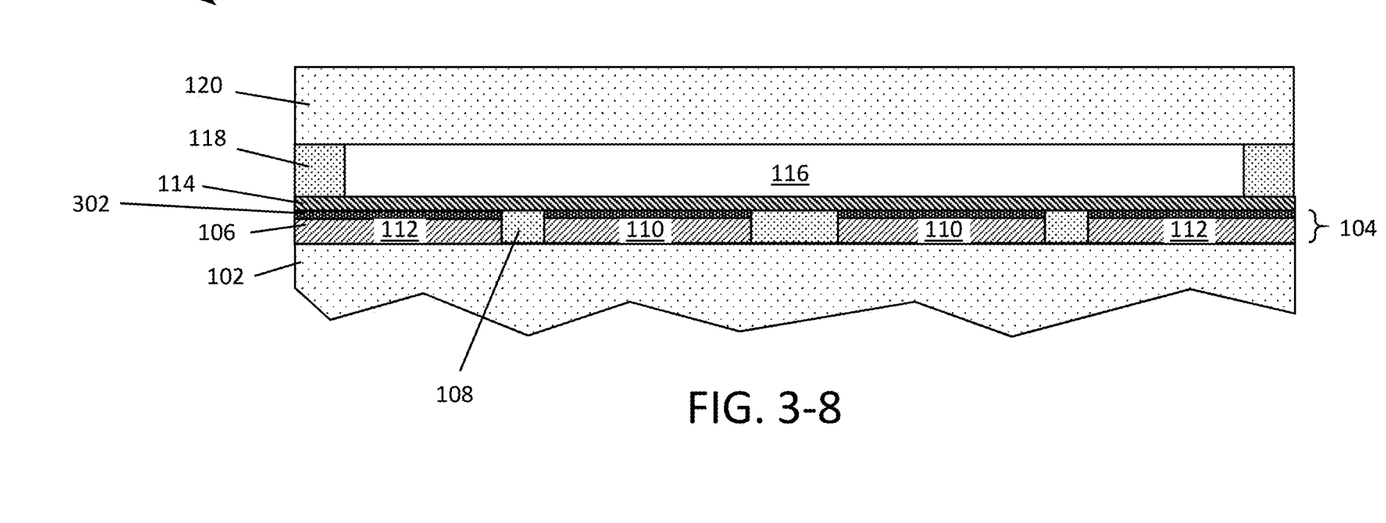

Proceeding to block 212 of FIG. 2, a micromachined ultrasonic transducer 100' is defined by etching the membrane support layer 118 to define a cavity 116 as shown in FIG. 3-7, followed by bonding a membrane layer 120 (e.g., highly doped silicon) having an exemplary thickness of about 2 μm to about 10 μm to the membrane support layer 118 to seal the cavity 116 as shown in FIG. 3-8. It should further be appreciated at this point that although the illustrated embodiments depict a single cavity, any suitable number of cavities and corresponding electrode structures may be formed (e.g., hundreds, thousands, tens of thousands, etc.) such that the CMOS substrate 102 may form part of a first semiconductor wafer and the membrane layer 120 may form part of a second semiconductor wafer bonded to the first semiconductor wafer so as to seal a number of such transducer cavities 116 (e.g., hundreds, thousands, tens of thousands, etc.).

Figure 4:
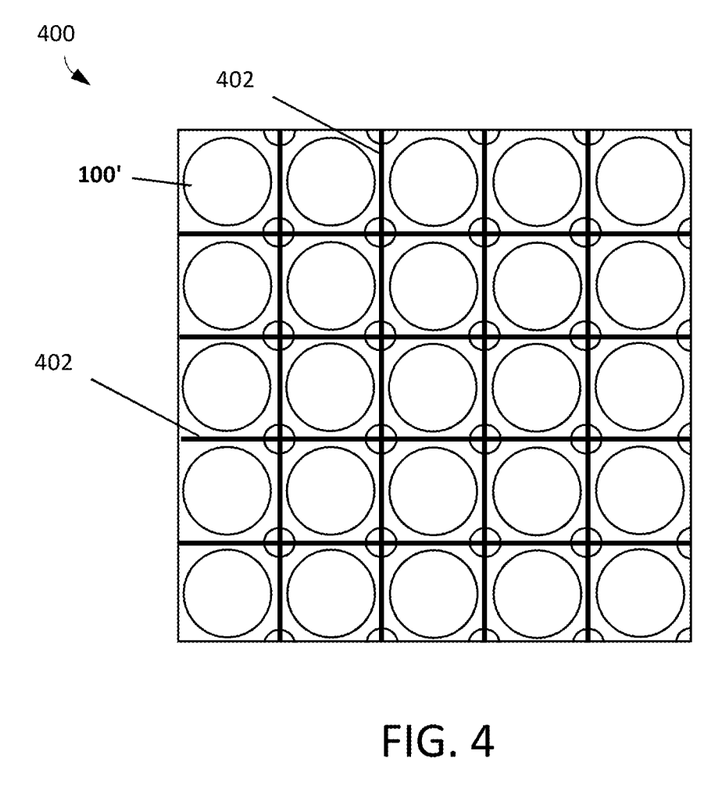
FIG. 4 is a top view of an example ultrasonic transducer device formed using the process flow of FIG. 2 and FIGS. 3-1 through 3-8.

FIG. 4 illustrates a top view of an example ultrasonic transducer device 400 formed using the exemplary process flow embodiments described herein. As illustrated, the transducer device includes an array of individual transducers 100', such as those described above. The specific number of transducers 100' shown in FIG. 4 should not be construed in any limiting sense, and may include any number suitable for a desired imaging application, which may be for example on the order of tens, hundreds, thousands, tens of thousands or more. FIG. 4 further illustrates an example location of metal 402 that may distribute an electrical signal to the membranes (upper electrodes) of the transducers 100'. It should also be appreciated that although the exemplary geometric structure of this portion of the ultrasonic transducer 100' is generally circular in shape, other configurations are also contemplated such as for example, rectangular, hexagonal, octagonal, and other multi-sides shapes, etc.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, some aspects of the technology may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method of forming an ultrasonic transducer device, the method comprising:
    forming a patterned metal electrode layer over a substrate, the patterned metal electrode layer comprising a lower layer and an upper layer formed on the lower layer;
    forming an insulation layer over the patterned metal electrode layer; and
    planarizing the insulation layer to the upper layer of the patterned metal electrode layer,
    wherein the upper layer comprises an electrically conductive material that serves as a chemical mechanical polishing (CMP) stop layer that has CMP selectivity with respect to the insulation layer and the lower layer, and wherein the upper layer has a CMP removal rate of about 100 times to about 200 times slower than that of the insulation layer.

2. The method of claim 1, wherein the upper layer comprises one of ruthenium (Ru) or tantalum (Ta).

3. The method of claim 2, wherein the upper layer comprises ruthenium (Ru).

4. The method of claim 2, wherein the lower layer comprises titanium (Ti).

5. The method of claim 4, wherein the insulation layer comprises SiO2.

6. The method of claim 5, wherein the $SiO_2$ layer is formed to an initial thickness of about 400 nanometers (nm) to about 900 nm before planarizing.

7. The method of claim 1, wherein the lower layer has a thickness of about 100 nm to about 300 nm, and the upper layer has a thickness of about 10 nm to about 30 nm.

8. The method of claim 1, further comprising:
forming a membrane support layer over the patterned metal electrode layer;
etching a cavity in the membrane support layer; and
bonding a membrane to the membrane support layer to seal the cavity.

9. The method of claim 8 wherein the membrane support layer comprises $SiO_2$ and the membrane comprises doped silicon.

10. The method of claim 9, wherein the membrane support layer has a thickness of about 100 nm to about 300 nm, and the membrane has a thickness of about 2 microns (μm) to about 10 μm.

11. The method of claim 8, further comprising forming a bottom cavity layer between the patterned metal electrode layer and the membrane support layer.

12. The method of claim 11, wherein the bottom cavity layer comprises a chemical vapor deposition (CVD) $SiO_2$ layer and an atomic layer deposition (ALD) $Al_2O_3$ layer formed on the $SiO_2$ layer.

13. The method of claim 12, wherein the CVD $SiO_2$ layer has a thickness of about 10 nm to about 30 nm and the ALD $Al_2O_3$ layer has a thickness of about 20 nm to about 40 nm.

14. A method of forming an ultrasonic transducer device, the method comprising:
forming a bi-metal transducer lower electrode layer over a complementary metal oxide semiconductor (CMOS) substrate, the lower electrode layer comprising a titanium (Ti) layer of 100 nanometers (nm) to 300 nm formed on the CMOS substrate and a ruthenium (Ru) layer of 10 nm to 30 nm formed on the Ti layer;
etching the bi-metal transducer lower electrode layer to form a patterned metal electrode layer;
forming an $SiO_2$ insulation layer of 400 nm to 900 nm over the patterned metal electrode layer;
planarizing the $SiO_2$ insulation layer to the Ru layer, wherein the Ru layer serves as a chemical mechanical polishing (CMP) stop layer that has CMP selectivity with respect to the $SiO_2$ and the Ti layer;
forming a bottom cavity layer over the between the patterned metal electrode layer, the bottom cavity layer comprising a chemical vapor deposition (CVD) $SiO_2$ layer having a thickness of 10 nm to 30 nm and an atomic layer deposition (ALD) $Al_2O_3$ layer having a thickness of 20 nm to 40 nm formed on the $SiO_2$ layer;
forming a membrane support layer over the bottom cavity layer, the membrane support layer comprising an $SiO_2$ layer having a thickness of 100 nm to 300 nm;
etching a cavity in the membrane support layer; and
bonding a membrane to the membrane support layer to seal the cavity, the membrane comprising doped silicon having a thickness of 2 microns (μm) to 10 μm,
wherein the Ru layer has a CMP removal rate of 100 times to 200 times slower than that of the $SiO_2$ insulation layer.

15. An ultrasonic transducer device, comprising:
a patterned metal electrode layer disposed on first regions of a substrate, the patterned metal electrode layer comprising a lower layer and an upper layer formed on the lower layer;
a planarized insulation layer disposed on second regions of the substrate layer, wherein the upper layer comprises an electrically conductive material that has CMP selectivity with respect to the insulation layer and the lower layer, and wherein the upper layer has a CMP removal rate slower than that of the insulation layer;
a cavity defined in a membrane support layer, the membrane support layer formed over the patterned metal electrode layer and the planarized insulation layer; and
a membrane bonded to the membrane support layer,
wherein the upper layer has a CMP removal rate of about 100 times to about 200 times slower than that of the insulation layer.

16. The device of claim 15, wherein the upper layer comprises one of ruthenium (Ru) or tantalum (Ta).

17. The device of claim 16, wherein the upper layer comprises ruthenium (Ru).

18. The device of claim 16, wherein the lower layer comprises titanium (Ti).

19. The device of claim 18, wherein the insulation layer comprises $SiO_2$.

20. The device of claim 15, wherein the lower layer has a thickness of about 100 nm to about 300 nm, and the upper layer has a thickness of about 10 nm to about 30 nm.

21. The device of claim 15, wherein the membrane support layer comprises $SiO_2$ and the membrane comprises doped silicon.

22. The device of claim 21, wherein the membrane support layer has a thickness of about 100 nm to about 300 nm, and the membrane has a thickness of about 2 microns (m) to about 10 μm.

23. The device of claim 15, further comprising a bottom cavity layer disposed between the patterned metal electrode layer and the membrane support layer.

24. The device of claim 23, wherein the bottom cavity layer comprises a chemical vapor deposition (CVD) $SiO_2$ layer and an atomic layer deposition (ALD) $Al_2O_3$ layer formed on the $SiO_2$ layer.

25. The device of claim 24, wherein the CVD $SiO_2$ layer has a thickness of about 10 nm to about 30 nm and the ALD $Al_2O_3$ layer has a thickness of about 20 nm to about 40 nm.

26. An ultrasonic transducer device, comprising:
a patterned bi-metal transducer lower electrode layer formed on first regions of a complementary metal oxide semiconductor (CMOS) substrate, the lower electrode layer comprising a titanium (Ti) layer of 100 nanometers (nm) to 300 nm formed on the first regions of the CMOS substrate and a ruthenium (Ru) layer of 10 nm to 30 nm formed on the Ti layer;
a planarized $SiO_2$ insulation layer of 400 nm to 900 nm formed on second regions of the CMOS substrate, wherein the Ru layer serves as a chemical mechanical polishing (CMP) stop layer that has CMP selectivity with respect to the SiO$_2$ and the Ti layer;

a bottom cavity layer formed over the between the patterned metal electrode layer, the bottom cavity layer comprising a chemical vapor deposition (CVD) SiO$_2$ layer having a thickness of 10 nm to 30 nm and an atomic layer deposition (ALD) Al$_2$O$_3$ layer having a thickness of 20 nm to 40 nm formed on the SiO$_2$ layer;

a membrane support layer formed over the bottom cavity layer, the membrane support layer comprising an SiO$_2$ layer having a thickness of 100 nm to 300 nm;

a cavity defined in the membrane support layer; and a membrane bonded to the membrane support layer to seal the cavity, the membrane comprising doped silicon having a thickness of 2 microns (μm) to 10 μm, wherein the Ru layer has a CMP removal rate of 100 times to 200 times slower than that of the SiO$_2$ insulation layer.

* * * * *